US008624031B2

(12) United States Patent
Wang et al.

(10) Patent No.: US 8,624,031 B2
(45) Date of Patent: Jan. 7, 2014

(54) PRODUCTION OF ALKALOIDS WITHOUT THE ISOLATION OF INTERMEDIATES

(75) Inventors: Peter X. Wang, Creve Coeur, MO (US); Tao Jiang, Chesterfield, MO (US); David W. Berberich, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 13/606,370

(22) Filed: Sep. 7, 2012

(65) Prior Publication Data

US 2013/0066080 A1 Mar. 14, 2013

Related U.S. Application Data

(60) Provisional application No. 61/532,253, filed on Sep. 8, 2011.

(51) Int. Cl.
*C07D 489/02* (2006.01)

(52) U.S. Cl.
USPC .......................................................... 546/45

(58) Field of Classification Search
None
See application file for complete search history.

(56) References Cited

U.S. PATENT DOCUMENTS

| 2,772,270 | A | 11/1956 | Weiss |
| 3,438,989 | A | 4/1969 | Shavel, Jr. et al. |
| 3,717,643 | A | 2/1973 | Archer |
| 4,089,855 | A | 5/1978 | Chatterjie et al. |
| 4,368,326 | A | 1/1983 | Rice |
| 4,443,605 | A | 4/1984 | Kotick et al. |
| 4,521,601 | A | 6/1985 | Rice |
| 4,673,679 | A | 6/1987 | Aungst et al. |
| 4,775,759 | A | 10/1988 | Rice et al. |
| 4,795,813 | A | 1/1989 | Schwartz |
| 4,912,114 | A | 3/1990 | Revesz |
| 4,991,391 | A | 2/1991 | Kosinski |
| 5,240,933 | A | 8/1993 | Merz et al. |
| 5,336,483 | A | 8/1994 | de Costa et al. |
| 5,668,285 | A | 9/1997 | Rice et al. |
| 5,693,820 | A | 12/1997 | Helmchen et al. |
| 5,739,145 | A | 4/1998 | Nagase et al. |
| 5,756,745 | A | 5/1998 | Kavka |
| 6,174,891 | B1 | 1/2001 | Nagase et al. |
| 6,184,381 | B1 | 2/2001 | Ikariya et al. |
| 6,277,859 | B1 | 8/2001 | Nagase et al. |
| 6,509,467 | B1 | 1/2003 | Blacker et al. |
| 6,887,999 | B1 | 5/2005 | Likhotvorik |
| 7,045,646 | B2 | 5/2006 | Tanis et al. |
| 7,932,264 | B2 | 4/2011 | Wang et al. |
| 8,252,808 | B2 | 8/2012 | Wang et al. |
| 8,269,006 | B2 | 9/2012 | Hudson et al. |
| 2004/0077863 | A1 | 4/2004 | Scammells et al. |
| 2004/0204434 | A1 | 10/2004 | Shafer et al. |
| 2005/0038250 | A1 | 2/2005 | Linders et al. |
| 2005/0182258 | A1 | 8/2005 | Schmidhammer et al. |
| 2006/0182692 | A1 | 8/2006 | Fishburn et al. |
| 2007/0265293 | A1 | 11/2007 | Boyd et al. |
| 2008/0161570 | A1 | 7/2008 | Perez et al. |
| 2008/0176884 | A1 | 7/2008 | Perez et al. |
| 2008/0207669 | A1 | 8/2008 | Perez et al. |
| 2008/0214817 | A1 | 9/2008 | Dlubala |
| 2008/0234306 | A1 | 9/2008 | Perez et al. |
| 2008/0274119 | A1 | 11/2008 | Moss et al. |
| 2008/0318966 | A1 | 12/2008 | Wang et al. |
| 2009/0062544 | A1 | 3/2009 | Wakita et al. |
| 2010/0216996 | A1 | 8/2010 | Cantrell et al. |

FOREIGN PATENT DOCUMENTS

| CH | 683 005 A5 | 12/1993 |
| CN | 1115318 | 1/1996 |
| CN | 1115318 A | 1/1996 |
| DE | 922 827 | 1/1955 |
| DE | 1119284 | 12/1961 |
| EP | 0 034 480 | 8/1981 |
| EP | 0 158 476 | 10/1985 |
| EP | 0 168 686 | 1/1986 |
| EP | 0 418 591 | 3/1991 |
| EP | 0 879 823 | 11/1998 |
| EP | 0 916 637 | 4/2005 |
| FR | 1 602 610 | 1/1971 |
| FR | 2 189 403 | 1/1974 |
| JP | 2001-302668 | 10/2001 |
| WO | WO 95/32973 | 12/1995 |
| WO | WO 98/05667 | 2/1998 |
| WO | WO 99/42105 | 8/1999 |
| WO | WO 01/14382 | 3/2001 |
| WO | WO 01/74819 | 4/2001 |
| WO | WO 2004/043964 | 5/2004 |
| WO | WO 2004/085058 | 10/2004 |
| WO | WO 2005/028483 | 3/2005 |
| WO | WO 2005/100361 | 10/2005 |
| WO | WO 2006/008562 | 1/2006 |
| WO | WO 2006/035195 | 4/2006 |
| WO | WO 2006/052710 | 5/2006 |
| WO | WO 2006/096626 | 9/2006 |
| WO | WO 2006/127899 | 11/2006 |
| WO | WO 2007/137785 | 12/2007 |
| WO | WO 2008/036172 | 3/2008 |

OTHER PUBLICATIONS

International Search Report of PCT/US2012/054099, Dec. 5, 2012, pp. 1-3.*

(Continued)

*Primary Examiner* — Zinna Northington Davis

(57) ABSTRACT

The invention relates to processes for the production of alkaloids without the isolation of intermediates.

9 Claims, No Drawings

(56) References Cited

OTHER PUBLICATIONS

Abdel-Magid et al., "Reductive Animation of Aldehydes and Ketones . . . ", Tetrahedron Letters, vol. 31, No. 39, 1990, p. 5395-5598.
Beyerman et al., "Synthesis of racemic and optically active codeine and morphine via the N-formylnordihydrothebainones", Journal of the Royal Netherlands Chemical Society, 97, 5, May 1978, pp. 127-130.
Beyerman et al., "Synthesis of racemic and of ( + )- and ( − )-1 methyldihydrothebainone. (Chemistry of opium alkaloids, Part IV)", Recl. Trav. Chim. Pays-Bas, 1976, 75, p. 184-188.
Bognar et al., Izvestiya po Khimiya, 1975, 81(1), p. 203-215.
Borch et al., "The cyanohydridoborate Anion as a Selective Reducing Agent", Journal of the American Chemical Society, 93:12, Jun. 16, 1971, p. 2897-2904.
Borch et al., "A New Method for the Methylation of Amines", J. Org. Chem., vol. 36, No. 10, 1972, pp. 1673-1674.
Brine et al., "Formamidinesulfinic Acid Reduction of Dihydrocodeinone Derivatives", J. Org. Chem., vol. 43, No. 8, 1978, p. 15551557.
Burke et al., "Probes for narcotic Receptor Mediated Phenomena . . . ", Heterocycles, vol. 23, No. 1, 1985, p. 99-110.
Butora et al., "Chemoenzymatic Synthesis of the Morphine Skeleton via Radical . . . ", Tetrahedron Letters, vol. 37, No. 45, 1996, p. 8155-8158.
Campbell et al., "The Preparation of Unsymmetrical Secondary Aliphatic Amines", Jan. 1944, vol. 66, p. 82-84.
Chatterjie et al., "Reduction of 6-Ketones of the Morphine Series . . . ", J. Org. Chem., vol. 41, No. 22, 1976, p. 3624-3625.
De Costa et al., "Probes for Narcotic Receptor Mediated Phenomena . . . ", J. Med. Chem., 19972, 35, p. 2826-2835.
Farber et al., "A Synthesis of Armepavine and Related Bases. Resolution of (±)-Armepavine", Anales. Asoc. Quim. Argentina, 58, 1970, pp. 133-138.
Farber et al., "Resolution of (±)-armepavine", Chemistry and Industry, Jan. 13, 1968, pp. 57-58.
Fujii et al., "The First Example of the Stereoselective Synthesis of . . . ", Chem. Pharm. Bull., 52(6), 2004, p. 747-750.
Fujii et al., "Ruthenium(II)-Caatalyzed Asymmetric Transfer . . . ", J. Am. Chem. Soc., 1996, 118, p. 2521-2522.
Gao et al., "Synthesis of 7-Arylmorphinans . . . ", J. Med. Chem., 1998, 41, p. 3901-3098.
Gorlitzer et al., "Diepoxy-bis-(iminoethano)-dinaphth[2,1-b: 1',2'-i]acridine $^{2,3+}$", Arch. Pharm. (Weinheim) 325, 1992, p. 637-641.
Greene et al., "Protection for Phenols", Protective Groups in Organic Synthesis, 3$^{rd}$, Ed., c1999, pp. 249-257and 266-269.
Gribble et al., "Reactions of Sodium Borohydride in Acidic Media . . . ", Communications, Aug. 1987, p. 709-711.
Hashiguchi et al., "Asymmetric Transfer Hydrogenation of Aromatic ketones Catalyzed by chiral Ruthenium(II) Complexes", J. Am. Chem. Soc., vol. 177, No. 28, 1995, p. 7562-7563.
Huang et al., "Synthesis of (+−)-Glaucine and (+−)-Neospirodienone via an One-Pot Bischler-Napieralski Reaction and Oxidative Coupling by a Hypervalent Iodine Reagent", Helvetica chimica Acta 2004 CH, vol. 887, No. 1, 2004, pp. 167-174, XP002476119.
Kalimin et al., "Palladium-Catalyzed 2-Phenylethenylation of Codeine . . . ", Helevetica Chimca Acta, vol. 89, 2006, p. 861-869.
Kametani et al., "131. Coclaurine 7-Benzyloxy-1,2,3,4-tetrahydro-1-(p-hydroxyphenyl)-6-methoxy-2-methylisoquinoline 7-Benzyloxy-1,2,3,4-tetrahydro-1-(p-hydroxybenzyl)-6-methoxy-2-methylisoquinoline", Coclaurine, vol. 87, No. 7, 1967, pp. 757-760.
Kashdan et al., "Synthesis of 1,2,3,4-Tetrahydroisoquinolines", J. Org. Chem., 1982, 47, pp. 2638-2643.
Kitamura et al., "General Asymmetric Synthesis of Isoquinoline Alkaloids. Enantioselective Hydrogenation of Enamides Catalyzed by BINAP-Ruthenium(II) Complexes", J. Org. Chem., 1994, 59, pp. 297-310.

Koolpe et al., "Opioid Agonists and Antagonists. 6-Desoxy-6-substituted . . . ", J. Med. Chem., 1985, 28(7), p. 949-957.
Klunenberg et al., "A Remarkable Influence of the Electrolyte in Andoic cyclization of 1-Benzyltetrahydroisoquinolines to neospirodienones or Morphinandienones", Tetrahedron Letters, 1982, vol. 23, No. 44, pp. 4581-4584.
Lau et al., "Evolution of a Series of Non-Quinoline Leukotriene $D_4$ Receptor Antagonist . . . ", Bioorganic & Medicinal chemistry Letters, vol. 5, No. 15, 1995, p. 1615-1620.
Lazar et al., "A Selective Removal of Benzyl Protecting Groups in Arylphosphate Esters with Bromotrimethylsilane", Synthetic Communications, 22(6), 1992, p. 923-931.
Leland et al., "Analgesic narcotic antagonists. 5. 7,7-Dimethyldihydrocodeinones . . . ", J. Med. Chem.., 1981, 24, p. 717-721.
Lespagnol et al., "Preparation of amides from the homoveratrylamine and iodephenylacetic substituted acids", Chim. Therap., 1965, pp. 14-16, English Translation by Fast-Trans.
Malspeis et al., "Metabolic Reduction of Naltrexone I. Synthesis, Separation . . . ", Res. Commun. Chem. Pathol. Pharmacal, 2(43), 1975.
Mao et al., "A Chiral Rhodium Complex for Rapid Asymmetric Transfer . . . ", Organic Letters, 1999, vol. 1, No. 6, p. 841-843.
Meuzelaar et al., "Chemistry of Opium Alkaloids, 45 Improvements in the Total Synthesis of Morphine", Eur. J. Org. Chem., 1999, pp. 2315-2321.
Nagase et al., "The Facility of Formation of a $\Delta^6$ Bond in Dihydromorphinone and Related Opiates", J. Org. Chem., 1989, 54, p. 4120-4125.
Nagata et al., "Synthetic Studies on Isoquinoline Alkaloids. I. An Efficient Synthesis of 9,10-Substituted Protoberberine Alkaloids", Chem. Pharm. Bull., 23(11), pp. 2867-2877, (1975).
Noyori et al., "Asymmetric Catalysts by Architechtural and Functional Molecular . . . ", Agew. Chem. Int., Ed. 2001, 40, p. 40-73.
Noyori et al., "Asymmetric Transfer Hydrogenation Catalyzed by Chiral Ruthenium Complexes", Acc. Chem. Res., 1997, 30, pp. 97-102.
Ohno et al., "Solid-Phase synthesis of 6-Sulfionylamino Morphinan Libraries", Synlett, 2002, No. 1, p. 93-96.
Olfason et al., "A New Reagent for the Selective, High-Yield N-Dealkylation of Teritary Amines: Improved Syntheses of Naltrexone and Nalbuphine", J. Org. Chem.., 1984, 49, p. 2081-2082.
Olieman et al., "Conversion of (−)-dihydrocodeinone into . . . ", Laboratory of Organic chemistry Technische Hogeschool Delft, Julianalaan 136, Delft, The Netherlands, Mar. 15, 1976.
Olsen et al., "Conjugate Addition Ligands of Opioid Antagonists . . . ", J. Med. Chem., 1990, 33(2), p. 737-741.
Palmer et al., "Asymmetric transfer hydrogenation of C=O and C=N bonds", Tetrahedron: Asymmetry 10, 1999, p. 2045-2061, XP 004174087.
Puntener et al., "New Efficient Catalysts for enantioselective Transfer Hydrogenations", Tet. Lett., 1996, 37(45), pp. 8165-8168.
Sagara et al., "Specific Affinity Labeling of . . . ", Bioorganic & Medicinal Chemistry Letters, vol. 5, No. 15, 1995, p. 1609-1614.
Saunders et al., "Assessment of relative nutritive value of proteins using streptoccus zymogenes", Chemistry and Industry, Jan. 13, 1968, pp. 56-58.
Schellenberg, "The Synthesis of Secondary and Tertiary Amines by Borohydride Reduction", Nov. 1963, p. 3259-3261.
Schmidhammer, "134. Synthesis and Biological ion of 14-Alkoxymorphinans Part 4) Opioid Agonists and Partial Opioid Agonists in a Series of . . . ", Helevitca Chimca Acta, vol. 72, 1989, p. 1233-1239.
Seki, "Studies on the Morphine Alkaloids . . . ", vol. 84, No. 7, p. 626-631, (1963).
Sheth et al., "Synthesis of N-(3',4'-Dimethoxy-5'-bromophenethyl)-2-(4"-hydrioxyphenyl)-acetamide & Allied Products", Indian Journal of Chemistry, vol. 15B, Jul. 1977, pp. 595-598.
Small et al., "The Addition of Organomagnesium Halides to Pseudocodeine Types. IV. Nuclear-Substituted Morphine Derivatives", Contribution from the Cobb Chemical Laboratory, University of Virginia, pp. 204-232.
Spadoni et al., "2[N-Acylamino($C_1$-$C_3$)alkyl]indoles as $MT_1$ . . . ", J. Med. Chem., 1998, 41, p. 3624-3634.

(56) References Cited

OTHER PUBLICATIONS

Tolkachev et al., "Synthetic Investigation in [Kurarealkaloidov] Area XVI. Synthesis 1-(e'-Bromine . . . ", Organicheskoi Khimii, 1966, 36(10), pp. 1767-1772, English Translation proviced by Fast-Trans.

Uba et al., "Stereospecific Synthesis of Codeine . . . ", Chem. Pharm. Bull., vol. 27, Issue 9, 1979, p. 2257-2258.

Uematsu et al., "Asymmetric Transfer Hydrogenation of Imines", J. Am. Chem. Soc., 1996, 118, p. 4916-4917.

Uwai et al., "Syntheses and receptor-binding studies of derivatives . . . ", Bioorganic & Medicinal Chemistry, 12, 2004, p. 417-421, XP 002488979.

H.C. van der Plas et al., "On the reaction of 2-, 3- and 4-bromo(chloro)-1,8-naphthyridine with potassium amide in liquid ammonia", Laboratory of Organic Chemistry, Agricultural University, Wagenagen, The Netherlands.

Van Gurp et al., "Synthesis of 7,8-Didehydro-3,4-Dimethoxy . . . ", Bull. Soc. Chim. Belg., vol. 96/n° Apr. 1987, p. 325-329.

Venkov et al., "Synthesis of isoquinolines from 2-phenylethylamines, amides, nitriles and carboxylic acids in polyphosphoric acid", Tetrahedron Sep. 9, 1996 GB, vol. 52, No. 37, Sep. 9, 1996, pp. 12299-12308, XP 002476120.

Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Watanabe et al., "Novel Synthesis of the Ortho Ester Derivative of 4,5-Epoxymorphinan", Organic Letters, vol. 8, No. 3, 2006, p. 523-526.

White et al., "Asymmetric Total Synthesis of (+)-Codeine via . . . ", J. Org. Chem., 1999, 64, p. 7871-7884.

White et al., "Asymmetric Synthesis of (+)-Morphine . . . ", J. Org. Chem., 1997, 62, p. 5250-5251.

Wu et al., "Asymmetric transfer hydrogenation of imines and iminiums . . . ", Chem. Commun., 2006, p. 1766-1768.

Yamakawa et al., "The Methal-Ligand Bifunctional Catalysis: A Theoretical Study on . . . ", J. Am. Chem. Soc., 2000, 122, p. 1466-1478.

Hitotsuyanagi et al., "Synthesis of an antitumor alkaloid sinocculine from sinomenine", Journal of the Chemical Society, Chemical Communications, 23, 1994, pp. 2707-2708, XP 009113662.

Hitotsuyanagi et al., "Syntheses of Antitumor Morphinane Alkaloids, Sinococuline and 6-epi-, 7-epi-, and 6-epi-7-sip-Sinococuline, from Sinomenine", Journal of Organic chemistry, 60(14), 1995, pp. 4549-4558, XP 002919264.

Hong et al., "Preparation of Opium Alkaloids by Palladium Catalyzed Bis-Cyclizations. Formal Total Synthesis of Morphine", Tetrahedron Letters, 35(21), 1994, pp. 3453-3456, XP 002376506.

\* cited by examiner

PRODUCTION OF ALKALOIDS WITHOUT THE ISOLATION OF INTERMEDIATES

CROSS REFERENCE TO RELATED APPLICATIONS

This application claims the benefit of U.S. Provisional Application No. 61/532,253 filed Sep. 8, 2011, which is incorporated herein in its entirety.

FIELD OF THE INVENTION

The present invention relates to improved processes for preparing alkaloids. The processes generally avoid the isolation of intermediate compounds produced in the multi-step synthesis of the alkaloid.

BACKGROUND OF THE INVENTION

Alkaloids are important pharmaceuticals that typically are used as analgesics or drug/alcohol cessation agents. Production of alkaloids generally proceeds through a number of synthetic steps, where each step requires isolation of the intermediate before the next synthetic step can be performed. Isolation becomes necessary for a number of reasons, including because byproducts of the reaction interfere with later synthetic steps which may lower the yield or halt the reaction altogether. Moreover, isolation of intermediates itself is an extra synthetic step that can lower the yield and efficiency of the total synthesis. The multi-step nature of the syntheses of the alkaloids described has limited their availability for commercial applications.

Thus, there is a need for routes to key alkaloids which do not require the isolation of intermediates.

SUMMARY OF THE INVENTION

The present invention relates to an improved process for preparing alkaloids without the isolation of intermediates.

In one aspect, the present invention provides a process for producing a compound comprising Formula (II) or salt thereof from a compound comprising Formula (I), wherein no intermediates are isolated. The process comprises (a) contacting a compound comprising Formula (I) with a ring forming agent and a proton donor to form a compound comprising Formula (V) (b) contacting the compound comprising Formula (V) with $R^{16}OCOX$ to form a compound comprising Formula (VI); and (c) contacting the compound comprising Formula (VI) with an hydrolysis agent to form the compound comprising Formula (II) according to the following reaction scheme:

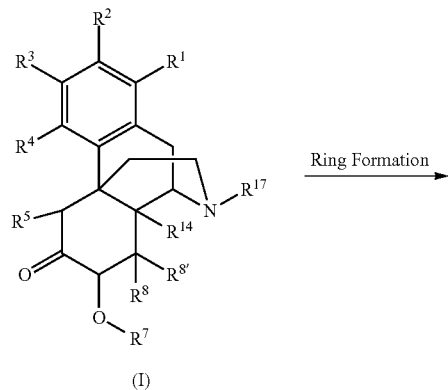

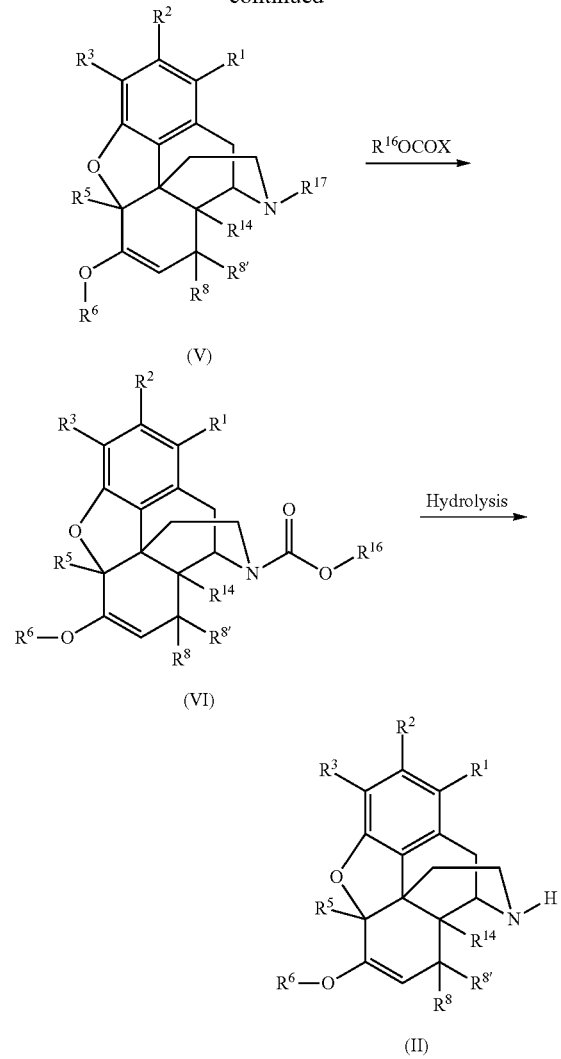

wherein, $R^1$, $R^2$, $R^3$, $R^5$, $R^8$, and $R^{8'}$ are independently chosen from hydrogen, hydrocarbyl, substituted hydrocarbyl, halogen, and $\{-\}OR^{15}$;

$R^4$ is $\{-\}OR^{15}$;

$R^6$, $R^7$, $R^{16}$, and $R^{17}$ are independently chosen from hydrogen, hydrocarbyl and substituted hydrocarbyl;

$R^{14}$ is chosen from hydrogen, and $\{-\}OR^{18}$;

$R^{15}$ is chosen from hydrogen, hydrocarbyl, and substituted hydrocarbyl; and

X is chosen from fluorine, chlorine, bromine, and iodine.

In yet another aspect, the invention provides a process for producing a compound comprising Formula (III) or salt thereof from the compound comprising Formula (I), wherein no intermediates are isolated. The process comprises (a) contacting a compound comprising Formula (I) with a ring forming agent and a proton donor to form a compound comprising Formula (V); (b) contacting the compound comprising Formula (V) with an agent containing a protecting group to form a compound comprising Formula (VII); (c) contacting the compound comprising Formula (VII) with $R^{16}OCOX$ to form a compound comprising Formula (VIII); (d) contacting the compound comprising Formula (VIII) with a hydrolysis agent to form the compound comprising Formula (IX); and (e) contacting the compound comprising Formula (IX) with a deprotecting agent to form the compound comprising Formula (II) according to the following reaction scheme:

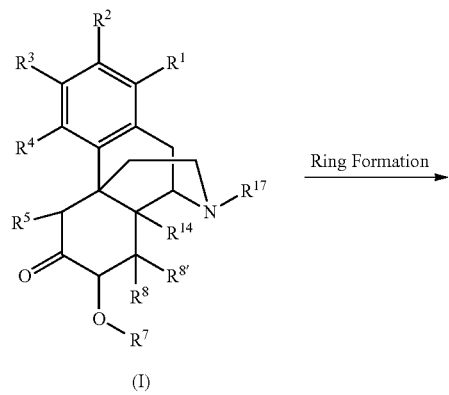

(I)

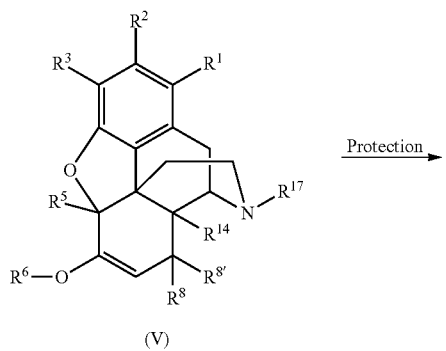

(V)

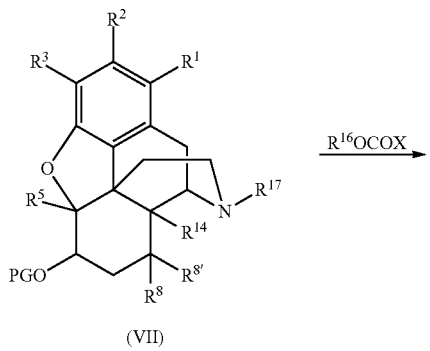

(VII)

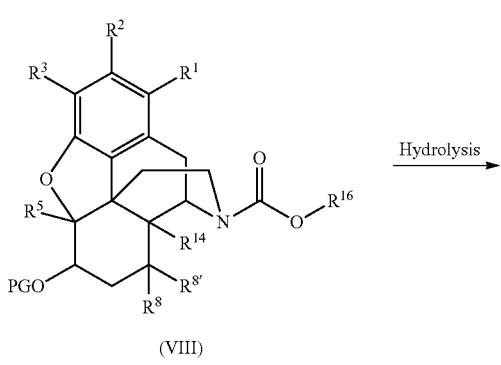

(VIII)

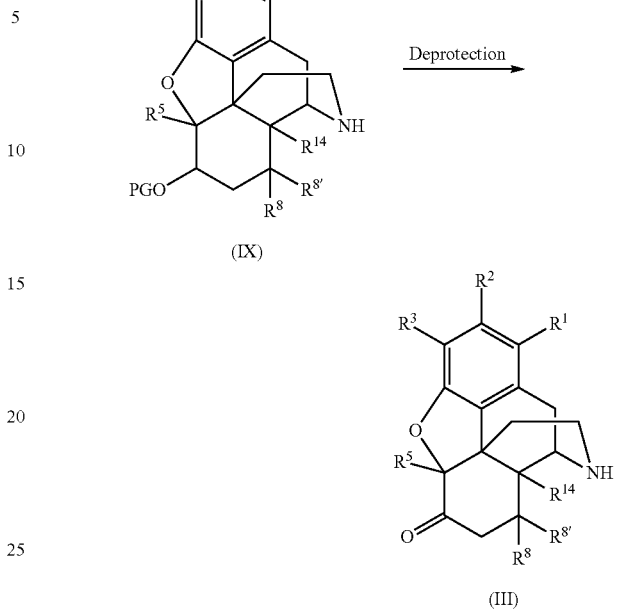

wherein,
$R^1$, $R^2$, $R^3$, $R^5$, $R^8$, and $R^{8'}$ are independently chosen from hydrogen, hydrocarbyl, substituted hydrocarbyl, halogen, and $\{-\}OR^{15}$;
$R^4$ is $\{-\}OR^{15}$;
$R^6$, $R^7$, $R^{16}$, and $R^{17}$ are independently chosen from hydrogen, hydrocarbyl and substituted hydrocarbyl;
$R^{14}$ is chosen from hydrogen, and $\{-\}OR^{15}$;
$R^{15}$ is chosen from hydrogen, hydrocarbyl, and substituted hydrocarbyl;
PG is a protecting group; and
X is chosen from fluorine, chlorine, bromine, and iodine.

In yet another embodiment, the invention provides a process for producing a compound comprising Formula (IV) or salt thereof from the compound comprising Formula (I), wherein no intermediates are isolated. The process comprises (a) contacting a compound comprising Formula (I) with a ring forming agent and a proton donor to form a compound comprising Formula (V); (b) contacting the compound comprising Formula (V) with a bromination reagent and an optional protecting group reagent to form a compound comprising Formula (X); and (c) contacting compound comprising Formula (X) with an elimination agent to form the compound comprising Formula (IV) according to the following reaction scheme:

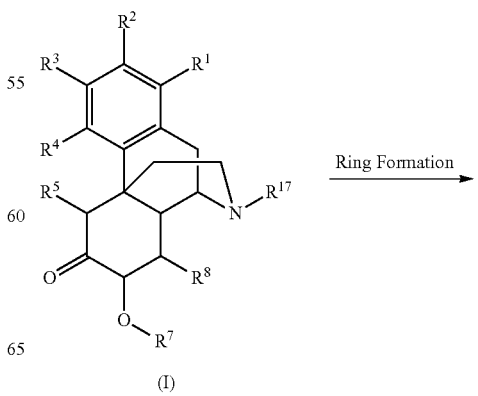

(I)

-continued

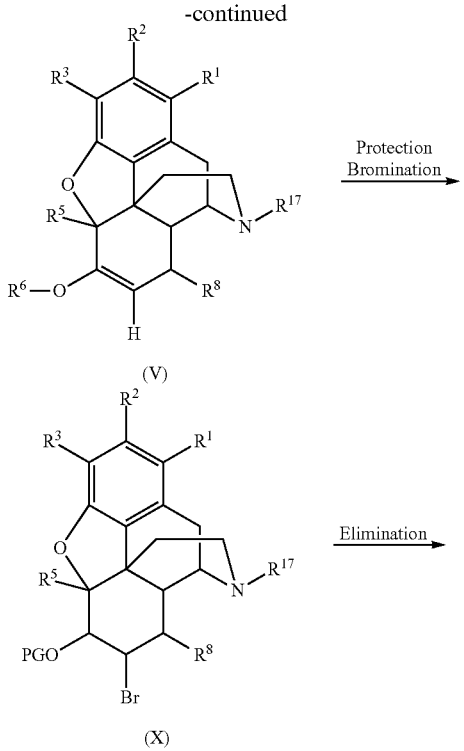

(V)

Protection
Bromination →

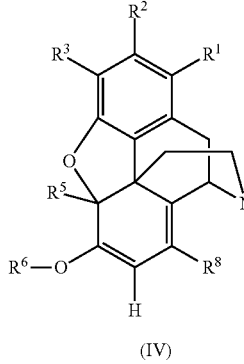

(X)

Elimination →

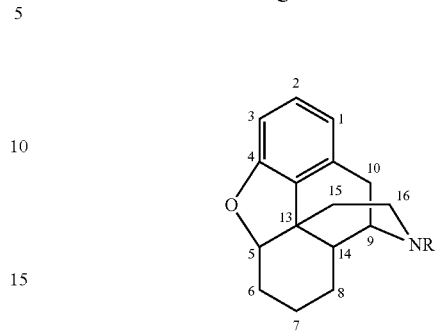

(IV)

wherein,
$R^1$, $R^2$, $R^3$, $R^5$, and $R^8$ are independently chosen from hydrogen, hydrocarbyl, substituted hydrocarbyl, halogen, and {—}$OR^{15}$;
$R^4$ is {—}$OR^{15}$;
$R^6$ and $R^{17}$ are chosen from hydrocarbyl and substituted hydrocarbyl;
$R^{15}$ is chosen from hydrogen, hydrocarbyl, and substituted hydrocarbyl; and
PG is a protecting group.
Other features and iterations of the disclosure are described in more detail herein.

DETAILED DESCRIPTION OF THE INVENTION

Briefly, therefore, the present invention relates to various syntheses of alkaloids wherein no intermediates are isolated. The choice of reagents, solvents, and extraction conditions avoid the need for the isolation of reaction intermediates. As used herein, a process where no intermediates are isolated means a process free of steps where intermediates are isolated from a reaction mixture on the synthetic pathway to form the desired alkaloid.

The products of the reaction generally comprise alkaloids which have the general structure below. The fused ring structure below shows the numbering associated with individual atoms of the alkaloid ring structure.

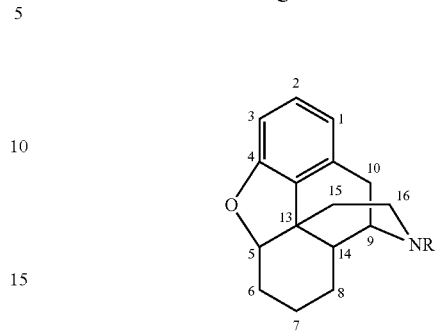

The core structure can be substituted as described herein and shown in various figures. The compounds described herein have stereocenters, and thus, each stereocenter may have and R or an S configuration such that both C-15 and C-16 are both on either the alpha face of the molecule, or both on the beta face of the molecule.

(I) Processes for Production of a Compound Comprising Formula (II)

In one embodiment, the present invention provides a process for producing a compound comprising Formula (II) or salt thereof from a compound comprising Formula (I). The reaction generally proceeds according to the following steps:

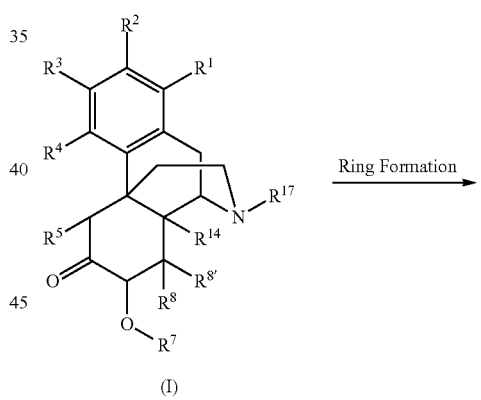

(I)

Ring Formation →

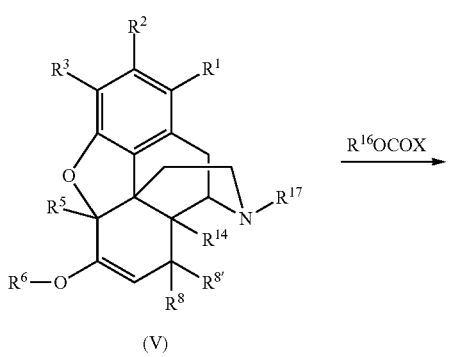

(V)

$R^{16}OCOX$ →

-continued

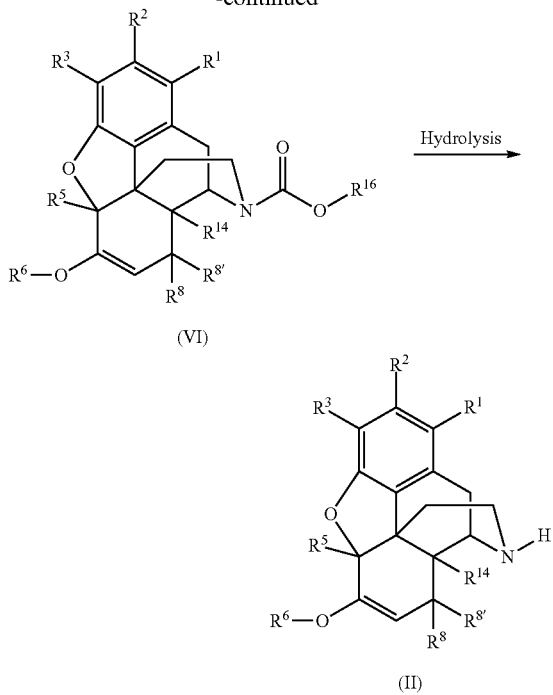

wherein no intermediates are isolated and, $R^1$, $R^2$, $R^3$, $R^5$, $R^8$, and $R^{8'}$ are independently chosen from hydrogen, hydrocarbyl, substituted hydrocarbyl, halogen, and {—}$OR^{15}$;

$R^4$ is {—}$OR^{15}$;

$R^6$, $R^7$, $R^{16}$, and $R^{17}$ are independently chosen from hydrogen, hydrocarbyl and substituted hydrocarbyl;

$R^{14}$ is chosen from hydrogen, and {—}$OR^{15}$;

$R^{15}$ is chosen from hydrogen, hydrocarbyl, and substituted hydrocarbyl; and

X is chosen from fluorine, chlorine, bromine, and iodine.

In one embodiment, $R^3$ is alkyl or alkoxy; and $R^6$, $R^7$, $R^{16}$, and $R^{17}$ are independently alkyl or substituted alkyl. In yet another aspect of the invention, $R^1$, $R^2$, $R^5$, $R^8$, $R^{8'}$, $R^{14}$, and $R^{15}$ are hydrogen; $R^3$ is {—}$OCH_3$; and $R^6$, $R^7$, and $R^{17}$ are methyl.

In still another embodiment, the compound comprising Formula (I) may be dihydrosinomenine, and the compound comprising Formula (II) may be (+)-nordihydrothebaine, where the configurations at the C-5, C-9, C-13, and C-14 are SSRS, respectively.

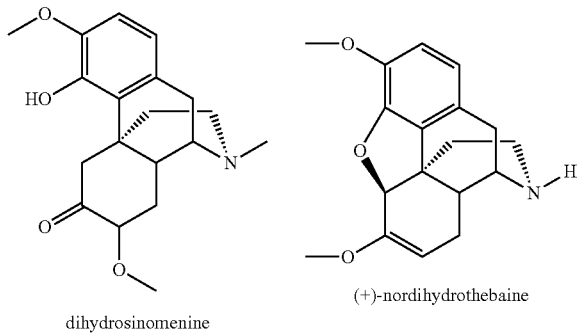

dihydrosinomenine           (+)-nordihydrothebaine (a) Formation of a Compound Comprising Formula (V) from the Compound Comprising Formula (I)

In the first step of the process, the compound comprising Formula (I) is contacted with a ring forming agent to form a compound comprising Formula (V) through five-membered ring formation. Ring formation of the compound comprising Formula (I) forms a 4,5-epoxy ring in the core structure.

(i) Reaction Mixture

The ring formation reaction comprises a ring forming agent chosen from orthoester reagents such as orthoformates or orthoacetates. Orthoformate compounds are of the general structure $CH(OR^{17})_3$, and orthoacetates are of the general formula $CCH_3(OR^{17})_3$, wherein $R^{17}$ groups are selected from hydrocarbyl groups. In an exemplary embodiment, $R^{17}$ groups are independently chosen from methyl and ethyl. In another exemplary embodiment, the ring forming agent is trimethyl orthoformate.

The molar ratio of the compound comprising Formula (I) to the orthoester can and will vary. In some embodiments, the ratio of the compound comprising Formula (I) to the orthoester ranges from about 1:0.9 to about 1:4. In other embodiments, the ratio of the compound comprising Formula (I) to the orthoester is about 1:0.9, or about 1:1, or about 1:1.5, or about 1:2, or about 1:2.5, or about 1:3, or about 1:3.5. In a preferred embodiment, the molar ratio of the compound comprising Formula (I) to the orthoester is about 1:2.

(ii) Proton Donor

The reaction mixture further comprise a proton donor. The proton donor generally has a pKa less than about 6. Suitable proton donors having this characteristic include, but are not limited to acetic acid, formic acid, methane sulfonic acid, phosphoric acid, sulfuric acid, hydrochloric acid, hydrobromic acid, hydroiodic acid, trifluoromethane sulfonic acid, toluenesulfonic acid, and the like. In a preferred embodiment, the proton donor is methane sulfonic acid.

The molar ratio of the compound comprising Formula (I) to the proton donor ranges from about 1:0.5 to about 1:5. In other embodiments, the ratio of the compound comprising Formula (I) to the proton donor is about 1:0.9, or about 1:1, or about 1:1.5, or about 1:2, or about 1:2.5, or about 1:3, or about 1:3.5, or about 1:4, or about 1:4.5, or about 1:5. In a preferred embodiment, the molar ratio of the compound comprising Formula (I) to the proton donor is about 1:3.

(iii) Solvent

The process may further comprise a solvent. The solvent for the reaction may be a polar, a non-polar organic solvent, or a combination thereof. Non-limiting examples of suitable polar organic solvents include acetonitrile, acetic acid, acetone, allyl alcohol, butyl acetate, n-butanol, chlorobenzene, chloromethane, cyclopentane, dichloromethane (DCM), dichloroethane, dimethyl formamide (DMF), dimethyl sulfonic acid (DMSO), 1,3-dimethyl-1,3,4,5,6-tetrahydro-2(1H)— pyrimidinone (DMPU), 1,3-dimethyl-2-imidizolinone (DMI), 1,2-dimethoxyethane (DME), dimethylacetamide (DMAC), ethanol, ethyl acetate, ethylene dichloride, ethylene bromide, fluorobenzene, hexamethylphosphoramide, isobutylmethylketone, isopropanol, isopropyl acetate, methanol, N-methylpyrrolidinone (NMP), methylene bromide, methylethylketone, methylbutylether, methyltetrahydrofuran, pentyl acetate, propionitrile, n-propanol, n-propyl acetate, 1,2-propyldiol, tetrahydrofuran, tetrachloroethane, dichloroethane, and the like. Non-limiting examples of suitable non-polar organic solvents include benzene, chloroform cyclohexane, cyclopentane, diethyl ether, dioxane, heptane, hexane, pentane, toluene, xylene, and the like. In some embodiments, the solvent may comprise a mixture of two solvents. When one or more organic solvents are present in the reaction the solvents may be present in any ratio without limitation. In some embodiments, one or more solvents may be present in the reaction in approximately an equal ratio by volume. In another embodiment, one solvent may be present in an excess. Where there are two solvents, the solvents may be present in a volume to volume (v/v) ratio of about 1:0.01, 1:0.1, 1:0.5, 1:0.9, 1:1, 1:1.5, 1:2, or 1:3. In an exemplary embodiment, the solvent may comprise a mixture of acetonitrile and methanol. In a preferred embodiment, the organic solvent may comprise a 1:0.1 v/v mixture of acetonitrile and methanol, respectively.

The amount of solvent added to the reaction mixture can and will vary. In general, the weight ratio of the solvent to the compound comprising Formula (I) may range from about 1:1 to about 100:1. In various embodiments, the weight ratio of the solvent to the compound comprising Formula (I) may range from 1:1 to about 5:1, from about 5:1 to about 25:1, or from about 25:1 to about 100:1. In exemplary embodiments, the weight ratio of the solvent to the compound comprising Formula (I) may range from about 5:1 to about 20:1.

(iv) Reaction Conditions

The conditions for the reaction between the compound comprising Formula (I) and the orthoester can vary without departing from the scope of the invention. In some embodiments, the reaction may be performed at a temperature ranging from about 40° C. to about 80° C. In alternate embodiments, the reaction may be conducted at about 45° C., about 50° C., about 60° C., or about 70° C. In a preferred embodiment, the reaction may be performed at about 63° C. The timing of the reaction can and will vary. In some embodiments, the reaction may be conducted over the course of about 30 minutes. In still other embodiments, the reaction may be conducted over the course of about 5 hours. In a preferred embodiment, the reaction may be conducted over the course of about 3 hours.

The yield of the compound comprising Formula (V) can and will vary. In general, the yield of the compound comprising Formula (V) is at least 40%. In various embodiments, the yield of the compound comprising Formula (V) may be at least 50%, at least 60%, at least 70%, at least 80%, or at least 90%.

(v) Extraction

Upon completion of the reaction of this step, the reaction mixture may undergo further processing. For example, the volume of the solvent may be reduced. The solvent may be reduced by any means known in the art including vacuum reduction, distillation, decanting and the like. In a preferred embodiment, the solvent is reduced with distillation. The reaction may further comprise the addition of solvents to increase the solvent volume. The reaction may be conducted with an amount of solvent ranging from about 0.2 L of solvent per mole of the compound comprising Formula (I) to about 5 L of solvent per mole of the compound comprising Formula (I). In one embodiment, the reaction is begun with about 1 L to about 2 L of solvent per mole of the compound comprising Formula (I), which is then reduced to about 0.2 L to about 0.5 L by distillation. In some embodiments, the process of adding solvents and reducing the volume of the solvents may be repeated one or more times.

The process may also comprise the removal of water. Water can be removed by various means including by water scavengers, anhydrous reagents, or through distillation with a Dean-Stark apparatus. In a preferred embodiment, water is removed by a Dean-Stark apparatus as reduction of solvent is occurring by distillation.

The process may further comprise one or more solvent extractions. The process for conducting an extraction between phases is known within the art, for example in Morhig, et al., Techniques in Organic Chemistry, W.H. Freeman and Co. NY, N.Y. (2003). Generally, when two immiscible solvents are mixed, they form a two phase solution. Compounds within the solvents tend to migrate toward the solvent which they have a greater solubility, thus, compounds can be selectively transported from one solvent to another. Additional reagents may further facilitate this movement by modifying the solubility characteristics of the compounds.

In some embodiments, extraction may be performed with the solvent used in the reaction. In other embodiments, the solvent used in the reaction is reduced, and one or more extraction solvents may be added. Preferably, the solvent for extraction is immiscible with water. By immiscible, it is meant that upon addition of the solvent to water, two phases are produced. Non-limiting examples of specific organic solvents that are generally immiscible with water include benzene, chlorobenzene, chloroform, cyclohexane, cyclopentane, dichloromethane (DCM), dichloroethane, diethyl ether, ethyl acetate, ethylene dichloride, ethylene bromide, fluorobenzene, heptane, hexane, isobutylmethylketone, N-methylpyrrolidinone (NMP), methylene bromide, methylethylketone, methylbutylether, pentyl acetate, pentane, n-propyl acetate, tetrachloroethane, toluene, trichloroethane, and xylene. In some embodiments, the extraction solvent is selected from chlorobenzene, chloroform, and toluene. In a preferred embodiment, the extraction solvent is toluene.

In one embodiment, a proton acceptor may be added to the extraction mixture. The proton acceptor generally has a pKa greater than about 7, or from about 7 to about 13, or more preferably from about 8 to about 10. Representative proton acceptors include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N—N-dimethylaminopyridine), and mixtures thereof. In some embodiments, the proton acceptor may be stabilized by a suitable counterion such as lithium, potassium, sodium, calcium, magnesium, and the like. In a preferred embodiment, the proton acceptor is sodium hydroxide.

The amount of proton acceptor added to the reaction mixture can and will vary. In some embodiments, the amount of proton acceptor is determined with respect to the starting molar amount of the compound comprising Formula (I) used in the reaction to form the compound comprising Formula (V). In some embodiments, the molar ratio between the starting amount of the compound comprising Formula (I) and the proton acceptor ranges from about 1:1 to about 1:40. In other embodiments, the molar ratio between the starting amount of the compound comprising Formula (I) and the amount of proton acceptor ranges from about 1:4 to about 1:10. In yet another embodiment, the molar ratio between the starting amount of the compound comprising Formula (I) and the proton acceptor is about 1:4, or 1:5, or 1:6, or 1:7, or 1:8. In a preferred embodiment, the molar ratio between the starting amount of the compound comprising Formula (I) and the proton acceptor is about 1:6.

In some embodiments, the proton acceptor is present in an aqueous solution. In alternate embodiments, an aqueous solution is added separately from the proton acceptor. The concentration of the proton acceptor in the aqueous system can and will vary within the scope of the invention. In some embodiments, the concentration ranges from about 1 M and about 18 M. In other embodiments the concentration ranges from about 1 M to about 10 M. In a preferred embodiment, the concentration of the proton acceptor in the aqueous solution is about 5 M.

The organic layer resulting from the extraction contains the compound comprising Formula (V).

(b) Formation of a Compound Comprising Formula (VI) from the Compound Comprising Formula (V)

The next step of the process comprises contacting the compound comprising Formula (V) with a compound comprising $R^{16}OCOX$ to form a compound comprising Formula (VI). The reaction to form the compound comprising Formula (IV) may be conduced within the organic layer generated after production of the compound comprising Formula (V) as described in Section (I)(a). The reaction to form the compound comprising Formula (VI) may be conducted within the resulting organic layer obtained from the synthesis of the compound comprising Formula (V) without isolation of the compound comprising Formula (V).

The process may comprise the addition of a proton acceptor to the organic layer resulting from the synthesis of the compound comprising Formula (V).

(i) Proton Acceptor

In general, the proton acceptor may be selected from those described in Section (I)(a)(v). In a preferred embodiment, the proton acceptor is sodium bicarbonate.

The amount of the proton acceptor added to the organic layer can and will vary depending on the strength of the proton acceptor. In some embodiments, the proton acceptor is added in a ratio ranging from about 1:1 to about 1:10 of the starting amount of the compound comprising Formula (I) to the proton acceptor. In an alternate embodiment, the proton acceptor is added in a ratio ranging from about 1:2 to about 1:5 of the starting amount of the compound comprising Formula (I) to the proton acceptor. In a preferred embodiment, the proton acceptor is added in a ratio of about 1:2 of the starting amount of the compound comprising Formula (I) to the proton acceptor.

(ii) Compound Comprising $R^{16}OCOX$

For the compound comprising $R^{16}OCOX$, $R^{16}$ may be hydrocarbyl or substituted hydrocarbyl. In some embodiments, $R^{16}$ is a hydrocarbyl or substituted hydrocarbyl having from 1 to 20 carbons and may be branched, straight chain, or cyclic. In yet another embodiment, $R^{16}$ is alkyl or substituted alkyl. In general, the alkyl or substituted alkyl has from 1 to 6 carbons. In one embodiment, $R^{16}$ is chosen from methyl, ethyl, and propyl. X may be chosen from fluorine, chlorine, bromine, and iodine. In another embodiment, X is chosen from chlorine and bromine. In a preferred embodiment the compound comprising $R^{16}OCOX$ is ethyl chloroformate.

The compound comprising $R^{16}OCOX$ may be added to the reaction in a molar ratio ranging from about 1:1 to about 1:10 of the starting amount of the compound comprising Formula (I) to the compound comprising $R^{16}OCOX$. In an alternate embodiment, the compound comprising $R^{16}OCOX$ is added in a molar ratio ranging from about 1:2 to about 1:5 of the starting amount of the compound comprising Formula (I) to the compound comprising $R^{16}OCOX$. In a preferred embodiment, the compound comprising $R^{16}OCOX$ is added in a ratio of about 1:0.5 of the starting amount of the compound comprising Formula (I) to the compound comprising $R^{16}OCOX$.

(iii) Reaction Conditions

The conditions for the reaction with the compound comprising $R^{16}OCOX$ can and will vary. The reaction time may range from about 0.5 hours to about 5 hours. In some aspects of the invention the compound comprising $R^{16}OCOX$ may be added drop-wise over the course of about 1 hour.

Typically, the reaction may be conducted at a temperature ranging from about 0° C. to about 100° C. For instance, the reaction may be conducted at about 45° C., about 50° C., about 55° C., about 60° C., about 65° C., about 70° C., about 75° C., about 80° C., about 85° C., about 90° C., about 95° C., or about 100° C. In a preferred embodiment, the reaction may be conducted at a temperature of about 60° C.

The process may further comprise a solvent for the reaction of the compound comprising $R^{16}OCOX$. The solvent may be chosen, for example, from the solvents listed in Section (I)(a)(iii).

(iv) Extraction

Upon completion of the reaction, the reaction mixture may under go additional processing. In some embodiments, the reaction solvent selected from those listed in Section (I)(a)(iii) may be evaporated off and a solvent from the solvents listed in Section (I)(a)(v) may be added to form the organic layer for extraction. In other embodiments, the solvent used in the reaction may also comprise the organic layer for extraction. In some embodiments, the solvent for extraction is chosen from chlorobenzene, chloroform, and toluene. In a preferred embodiment, the solvent is toluene.

The organic layer may be treated with an aqueous solution and/or a proton donor. Suitable proton donors include those listed in Section (I)(a)(ii). Addition of an aqueous solution preferably gives a two phase solution for extraction. The process for conducting an extraction between phases is known within the art, for example in Morhig, et al, Techniques in Organic Chemistry, W.H. Freeman and Co. NY, N.Y. (2003).

In a preferred embodiment, the process comprises one extraction of the organic solution produced from the reaction with the compound comprising $R^{16}OCOX$ with water, followed by another extraction with an aqueous solution comprising a proton donor. In a preferred embodiment, the aqueous solution comprising a proton donor is a 1% solution of acetic acid in water.

The organic layer resulting from the extraction contains the compound comprising Formula (VI).

(C) Formation of a Compound Comprising Formula (II) from the Compound Comprising Formula (VI)

Formation of the compound comprising Formula (II) may proceed from the organic layer containing the compound comprising Formula (VI). The formation of the compound comprising Formula (II) generally comprises a hydrolysis reaction with a proton acceptor having a pKa greater than about 7. The proton acceptor may be selected from those listed in Section (I)(a)(v).

The amount of the proton acceptor added to the organic layer can and will vary depending on the strength of the proton acceptor. In some embodiments the proton acceptor is added in a molar ratio of 1:0.5 to 1:10 of the starting amount of the compound comprising Formula (I) to the proton acceptor. In an alternate embodiment, the proton acceptor is added in a ratio of about 1:1 to about 1:5 of the starting amount of the compound comprising Formula (I) to the proton acceptor. In a preferred embodiment, the proton acceptor is added in a molar ratio of about 1:2 of the starting amount compound comprising Formula (I) to the proton acceptor.

(i) Reaction Conditions

The process may further comprise one or more organic solvents for the reaction with the proton acceptor. The solvents may be selected from those listed in Section (I)(a)(iii). When one or more organic solvents are present in the reaction the solvents may be present in any ratio. In some embodiments, one or more solvents may be present in the reaction in approximately an equal ratio by volume. In another embodiment, one solvent may be present in an excess. Where there are two solvents, the solvents may be present in a v/v of about 1:0.01, 1:0.1, 1:0.5, 1:0.9, 1:1, 1:1.5, 1:2, or 1:3. In a preferred embodiment, the organic solvent comprises 1:1 v/v mixture of dimethyl sulfoxide and 1,2-propyldiol, respectively.

The reaction of the proton acceptor with the organic layer comprising the compound comprising Formula (VI) may be conducted at a variety of temperatures for a period of time sufficient to form the compound comprising Formula (II). In general, the reaction may be conducted for an amount of time ranging from about 1 hour to 5 hours. The reaction is generally run at a temperature ranging from about 60° C. and about 140° C. In some embodiments, the reaction is conducted at a temperature of about 100° C. to about 130° C. for about the first 3 hours of the reaction and at about 60° C. to about 80° C. for the remainder of the reaction.

The process may further comprise reduction of the solvent. The solvent may be reduced by any means known in the art including vacuum reduction, distillation, decanting and the like. In a preferred embodiment, the solvent is reduced with distillation.

(ii) Extraction

The process may further comprise an extraction as described in Section (I)(a)(v). In such embodiments, the organic layer from the extraction contains the compound comprising Formula (II).

In some aspects of the invention, the compound comprising Formula (II) is isolated by means known within the art including through chromatography, evaporation of the solvent, and the like.

(d) Formation of a Salt of the Compound Comprising Formula (II)

In one aspect of the invention, the compound comprising Formula (II) may be isolated as a salt of the compound comprising Formula (II). The salt form may be produced by reaction with a corresponding acid to form the alkaloid salt. In preferred embodiments, the salt is a pharmaceutically acceptable salt including, but not limited to hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpriopionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like.

The salt of the compound comprising Formula (II) may be isolated by methods known in the art. In one embodiment, the salt of the compound comprising Formula (II) may be isolated by precipitation followed by drying.

(e) Formation of a Compound Comprising Formula (III) from the Compound Comprising Formula (II)

In another aspect of the invention, the compound comprising Formula (II) or salt thereof may be converted to the compound comprising Formula (III) or salt thereof by contact with a hydrolysis agent. The structure of the compound comprising Formula (III) is presented below in section (II).

Hydrolysis of the compound comprising Formula (II) may be performed with or without isolation of the compound comprising Formula (II). Hydrolysis of the enolate to form the ketone may be performed by methods known in the art. Generally, the hydrolysis comprises water. The hydrolysis may further comprise a proton donor. Suitable proton donors may include those listed in Section(I)(a)(ii).

The salt of the compound comprising Formula (III) may be formed as described in Section (II)(e). The compound comprising Formula (III) or the salt of the compound comprising Formula (III) may be isolated by any means know in the art.

The yield and purity of the compounds comprising Formula (II), Formula (III), or the salts of either Formula (II) or (III) may vary depending on the reaction conditions. The yield generally ranges from about 40% to about 60%. In some embodiments, the yield may be above about 50%, or above 60%. The purity of the compound may vary. In some embodiments, the purity of the compounds is above about 85%, or above about 90%, or above about 95%.

In some embodiments, the processes may give the compounds in a particular configuration. The C-5, C-9, C-13, and C-14 carbons of the compounds comprising Formula (II), Formula (III), or the salts of either Formula (II) or (III) may be either (R) or (S), so long as both C-15 and C-16 are on the same face of the molecule. In one embodiment, the C-5, C-9, C-13, and C-14 stereocenters of the compound comprising Formula (II), Formula (III), or the salts of either Formula (II) or (III) are chosen from RRRR, RRRS, RRSR, RRSS, RSRS, RSRR, RSSR, RSSS, SRRR, SRRS, SRSR, SRSS, SSRS, SSRR, SSSR, and SSSS, respectively. In another aspect the C-5, C-9, C-13, and C-14 stereocenters of the compound comprising Formula (II), Formula (III), or the salts of either Formula (II) or (III) are chosen from RRSR, SRSR, RSRS, and SSRS, respectively. In another embodiment, the C-5, C-9, C-13, and C-14 stereocenters of the compound comprising Formula (II), Formula (III), or the salts of either Formula (II) or (III) are RRSR, respectively. In still another embodiment, the C-5, C-9, C-13, and C-14 stereocenters of the compound comprising Formula (II), Formula (III), or the salts of either Formula (II) or (III) are SSRS, respectively.

(II) Process for Producing the Compound Comprising Formula (III)

In yet another aspect of the invention, the process provides the production of a compound comprising Formula (III) from a compound comprising Formula (I), without the isolation of intermediates.

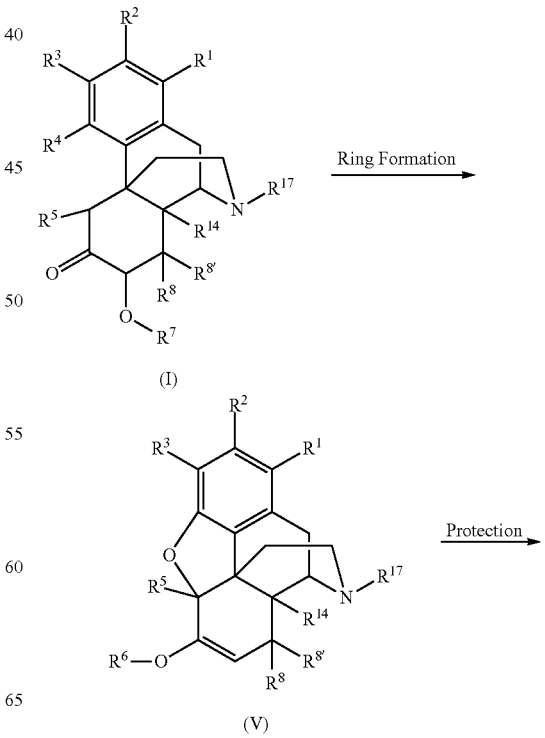

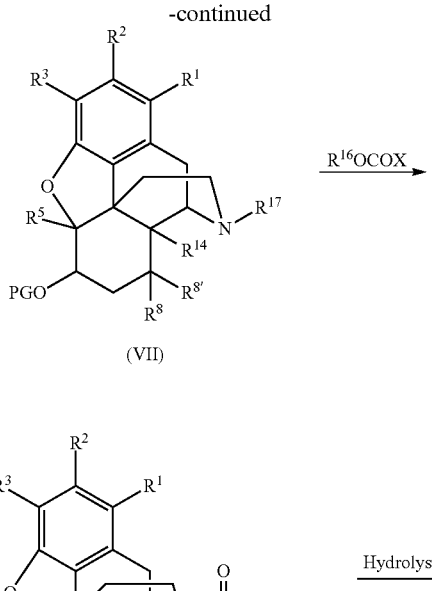

(VII)

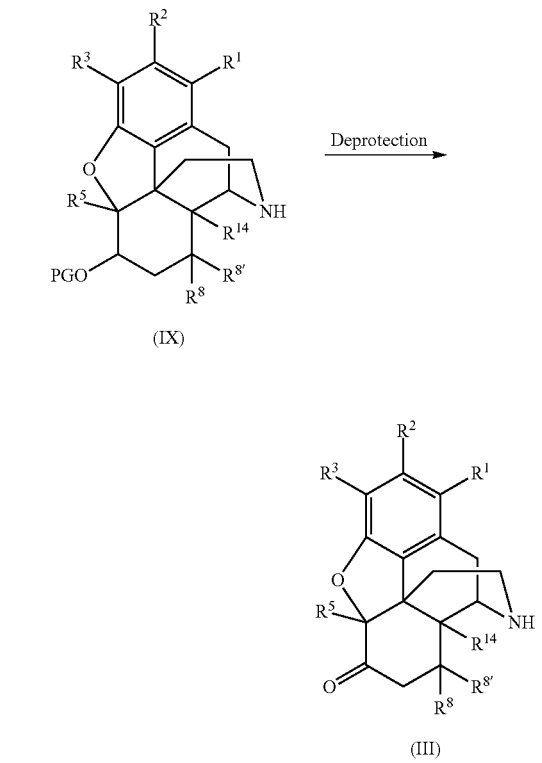

(VIII)

(IX)

(III)

wherein no intermediates are isolated, PG is a protecting groups, and the R groups are as defined above in section (I).

In one embodiment, $R^3$ is alkyl or alkoxy; and $R^6$, $R^7$, $R^{16}$, and $R^{17}$ are independently alkyl or substituted alkyl. In yet another aspect of the invention, $R^1$, $R^2$, $R^5$, $R^8$, $R^{8'}$, $R^{14}$, and $R^{15}$ are hydrogen; $R^3$ is {—}OCH$_3$; and $R^6$, $R^7$, and $R^{17}$ are methyl.

In still another aspect of the invention, the compound comprising Formula (I) is dihydrosinomenine and the compound comprising Formula (III) is (+)-norhydrocodone.

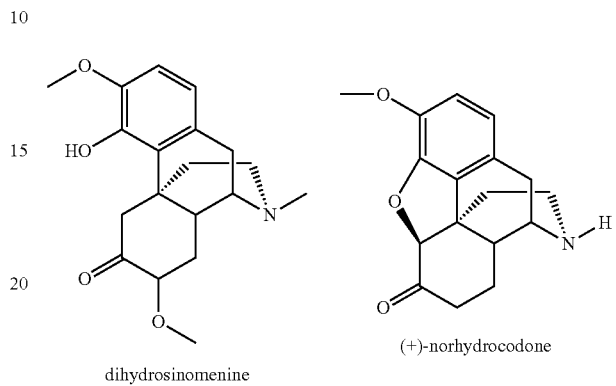

dihydrosinomenine (+)-norhydrocodone (a) Formation of a Compound Comprising Formula (V) from the Compound Comprising Formula (I)

In one embodiment, the compound comprising Formula (I) may be transformed to a compound comprising Formula (V) through ring formation of the compound comprising Formula (I) as described in Section (I)(a)(i)-(v).

(b) Formation of a Compound Comprising Formula (VII) from the Compound Comprising Formula (V)

A compound comprising Formula (VII) may be formed by the reaction of the organic layer resulting from the formation of the compound comprising Formula (V) with a suitable protecting group.

(i) Protecting Groups

In one aspect of the invention, the C-6 ketone group of the compound comprising Formula (V) is protected. Protection of the C-6 ketone moiety may be accomplished by a variety of methods known in the art. A variety of protecting groups and the synthesis thereof may be found in "Protective Groups in Organic Synthesis" by T. W. Greene and P. G. M. Wuts, John Wiley & Sons, Fourth Edition, 2007. Examples of carbonyl protecting groups include acetals, alkyls, ketals, cyclic acetals, cyclic ketals, mono- or dithioacetals, mono- or dithioketals, diols, silanes, hydrazones, substituted hydrazones or oximes. Examples of specific protecting groups include dimethyl acetal, S,S-dimethylthioacetal, 1,3-dioxolane, 1,3-dioxane, S,S'-dimethylketal, 1,3-dithiane, 1,3-dithiolane, 1,3-oxathiolane, N,N-dimethylhydrazone, 1,3-oxathiolane, 1,2-bis(trimethylsilyloxy)ethane, 1,2-ethane diol, propane 1,3-dial, and the like. In one embodiment, the protecting group is formed by reaction with 1,2-ethane diol.

In the reaction schemes, the carbonyl protecting group is represented by OPG. This represents that the protecting group is bound to at least one oxygen containing group. As will be appreciated by one of skill in the art, the protecting group may comprise further bonds with the compound being protected, for example through bonding with another C6 oxygen group. Illustrative examples of C6 carbonyl protecting groups are shown below on the core morphinan structure.

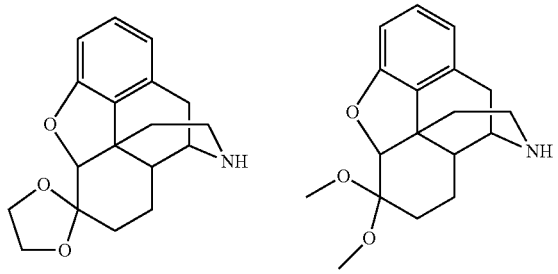 [SMILES: c1cc2c3c(c1)OC1C4(CCC5C(C2)NCCC351)OCCO4 ; COC1(OC)CCC2C3Cc4cccc5c4C2(CCN3)C1O5]

(ii) Reaction Conditions

The time and temperature of the protection reaction can vary depending on the protecting group chosen. In some embodiments, the reaction is performed at a temperature ranging from about 0° C. to about 80° C. In alternate embodiments, the reaction is conducted at about 0° C., about 10° C., about 20° C., about 30° C., about 40° C. or about 50° C. In a preferred embodiment, the reaction is performed at about 68° C. The timing of the reaction can and will vary. In some embodiments, the reaction may be conducted over the course of about 30 minutes. In still other embodiments, the reaction may be conducted over the course of about 5 hours. In a preferred embodiment, the reaction may be conducted over the course of about 3 hours.

The process may further comprise a solvent for the protection reaction. Non-limiting examples of solvents include those listed in Section (I)(a)(iii). In one embodiment the solvent is chosen from chlorobenzene, chloroform, and toluene. In a preferred embodiment, the solvent is toluene.

(iii) Extraction

In one embodiment, the resulting solution from the protection reaction is subjected to an extraction. The extraction may be conducted as described in Section (I)(a)(v). In one embodiment the solvent for extraction is chosen from chlorobenzene, chloroform, and toluene. In a preferred embodiment, the solvent is toluene.

(c) Formation of a Compound Comprising Formula (VIII) from the Compound Comprising (VII)

In another embodiment, the process provides a compound comprising Formula (VIII). The reaction to form the compound comprising Formula (VIII) may be conducted with the organic layer produced in the synthesis of the compound comprising Formula (VII). The reaction to form the compound comprising Formula (VIII) may be conducted on the organic layer resulting from the synthesis of the compound comprising Formula (VII) without isolation of the compound comprising Formula (VII).

Reaction with the compound comprising $R^{16}OCOX$ may be performed as described in Section (I)(b)(i)-(iv). The resulting organic layer contains the compound comprising Formula (VIII).

(D) Formation of a Compound Comprising Formula (IX) from the Compound Comprising (VIII)

The formation of a compound comprising Formula (IX) may proceed from the organic layer containing the compound comprising Formula (VIII). The organic layer containing the compound comprising Formula (VIII) may be used without isolation of the compound comprising Formula (VIII). The formation of the compound comprising Formula (IX) generally comprises reaction with a proton acceptor. The proton acceptor may be selected from those listed in Section (I)(b)(i). In a preferred embodiment, the proton acceptor is sodium hydroxide.

The amount of the proton acceptor added to the organic layer can and will vary depending on the strength of the proton acceptor. In some embodiments, the proton acceptor is added in a molar ratio ranging from about 1:1 to about 1:10 of the starting amount of the compound comprising Formula (I) to the proton acceptor. In an alternate embodiment, the proton acceptor is added in a molar ratio ranging from about 1:2 to about 1:5 of the starting amount of the compound comprising Formula (I) to the proton acceptor. In a preferred embodiment, the proton acceptor is added in a molar ratio of about 1:2 of the starting amount compound comprising Formula (I) to the proton acceptor.

(i) Reaction Conditions

The reaction with the proton acceptor may further comprise one or more organic solvents. The solvent or solvents may be selected from those listed in Section (I)(a)(iii). When one or more organic solvents are present in the reaction the solvents may be present in any ratio without limitation. In some embodiments, one or more solvents may be present in approximately an equal ratio by volume. In another embodiment, one solvent may be present in an excess. Where there are two solvents, the solvents may be present in a ratio of about 1:0.01, 1:0.1, 1:0.5, 1:0.9, 1:1, 1:1.5, 1:2, or 1:3 v/v. In a preferred embodiment, the organic solvent comprises a 1:1 v/v mixture of dimethyl sulfoxide and 1,2-propyldiol, respectively.

The reaction of the proton acceptor with the compound comprising Formula (VIII) may be conducted at a variety of temperatures for a period of time sufficient to form the compound comprising Formula (IX). In general, the reaction may be conducted for an amount of time ranging from about 1 hour to 10 hours. The reaction is generally run at a temperature ranging from about 40° C. to about 140° C. In some embodiments, the reaction is conducted at a temperature of about 100° C. to about 130° C. for about the first 3 hours of the reaction and at about 50° C. to about 80° C. for the remainder of the reaction.

(ii) Extraction

The process may further comprise an extraction as described in Section (I)(a)(v). In such embodiments, the organic layer from the extraction contains the compound comprising Formula (II).

(e) Formation of a Compound Comprising Formula (III) from the Compound Comprising Formula (IX)

In another aspect, the process provides a compound comprising Formula (III) by reaction of the compound comprising Formula (IX). The reaction to form the compound comprising Formula (III) may be conduced with the organic layer produced in the synthesis of the compound comprising Formula (IX). The reaction to form the compound comprising Formula (III) may be conducted on the resulting organic layer from the synthesis of the compound comprising Formula (IX) without isolation of the compound comprising Formula (IX).

The reaction to form the compound comprising Formula (III) may further comprise a proton donor. The proton donor may be chosen from those listed in Section (I)(a)(ii). In a preferred embodiment, the proton donor is sulfuric acid.

The proton donor is preferably present in an aqueous solution. The concentration of the proton donor in the aqueous system can and will vary within the scope of the invention. In some embodiments, the concentration ranges from about 1M and about 18 M. In other embodiments the concentration ranges from about 1M to about 10 M. In a preferred embodiment, the concentration of the proton donor in the aqueous solution is about 5 M.

(i) Reaction Conditions

The reaction may be performed at temperatures ranging from about 20° C. to about 100° C. In some embodiments, the reaction is performed at a temperature ranging from about 40° C. to about 80° C. For instance, the reaction may be conducted at a temperature of about 20° C., about 30° C., about 40° C., about 50° C., about 60° C., about 70° C., about 80° C., about 90° C., or about 100° C. The reaction is generally conducted under ambient temperatures. In a preferred embodiment, the reaction may be conducted at about 70° C.

(ii) Extraction

The reaction may further comprise one or more extractions between an organic layer and an aqueous layer as described in Section (I)(b)(iv).

In one aspect of the invention, the compound comprising Formula (III) may be isolated as the salt of the compound comprising Formula (III). The salt form may be produced by reaction with a corresponding acid to form the alkaloid salt, preferably a pharmaceutically acceptable alkaloid salt. In some embodiments the acid to form the pharmaceutically acceptable salts are selected from, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpriopionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like. The salt of the compound comprising Formula (III) may be isolated by any means know in the art, including by precipitation followed by drying.

The yield and purity of the compound comprising Formula (III) or the salt thereof may vary depending on the reaction conditions. The yield generally ranges from about 40% to about 70%. In some embodiments, the yield may be above about 50%. The purity of the compound may vary. In some embodiments, the purity of the compounds is above about 85%, or above about 90%, or above about 95%.

In some embodiments, the process produces compounds having a particular configuration. The C-5, C-9, C-13, and C-14 carbons of the compound comprising Formula (III) or the salts thereof may be either (R) or (S), so long as both C-15 and C-16 are on the same face of the molecule. In one embodiment, the C-5, C-9, C-13, and C-14 stereocenters of the compound comprising Formula (III) or the salts thereof is chosen from RRRR, RRRS, RRSR, RRSS, RSRS, RSRR, RSSR, RSSS, SRRR, SRRS, SRSR, SRSS, SSRS, SSRR, SSSR, and SSSS, respectively. In another embodiment, the C-5, C-9, C-13, and C-14 stereocenters of the compound comprising Formula (III) or the salts thereof is chosen from RRSR, SRSR, RSRS, and SSRS, respectively. In another embodiment, the C-5, C-9, C-13, and C-14 stereocenters of the compound comprising Formula (III) or the salt thereof are RRSR, respectively. In yet another embodiment, the C-5, C-9, C-13, and C-14 stereocenters of the compound comprising Formula (III) or the salt thereof are SSRS, respectively.

(III) Process for Producing a Compound Comprising Formula (IV)

In another aspect of the invention, the process provides a compound comprising Formula (IV) from the compound comprising Formula (I) without the isolation of intermediates.

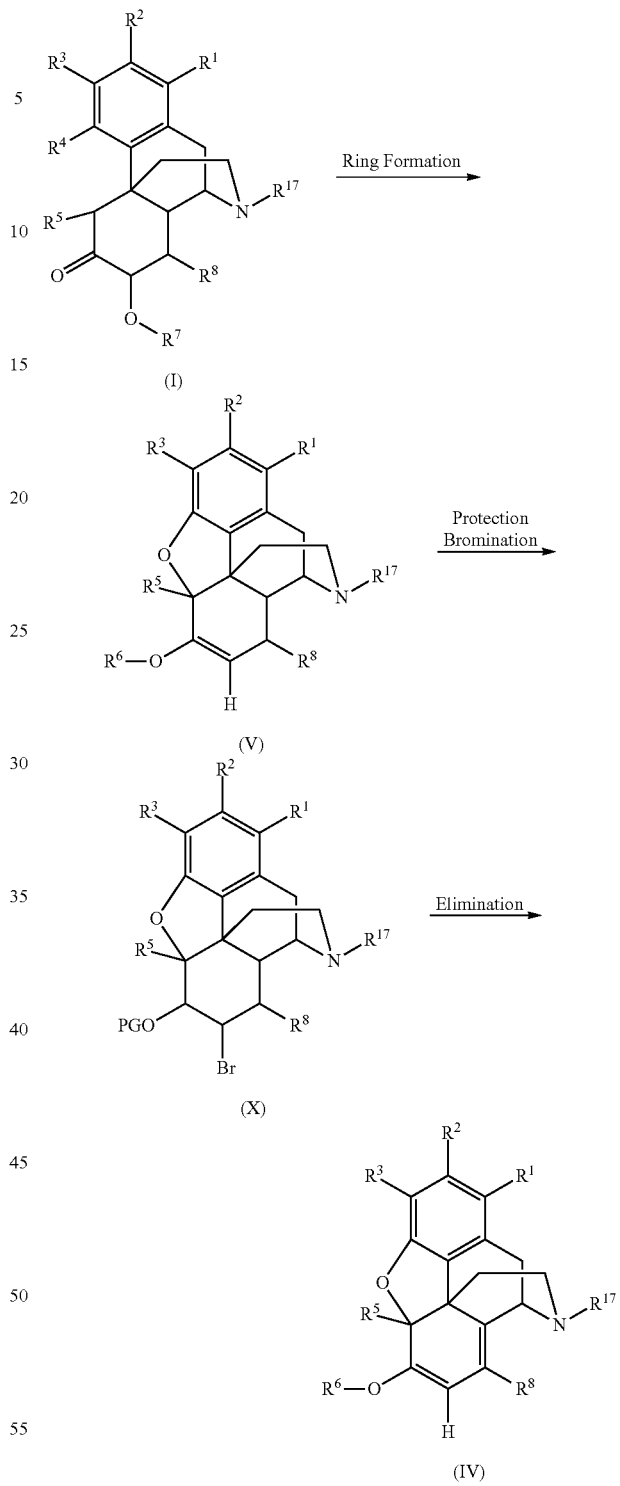

wherein no intermediates are isolated, PG is a protecting group, and the R groups are as defined in section (I) with the exception that $R^6$ and $R^{17}$ are chosen from hydrocarbyl and substituted hydrocarbyl.

In one embodiment, $R^3$ is alkyl or alkoxy; and $R^6$, $R^7$, and $R^{17}$ are independently alkyl or substituted alkyl. In yet another aspect of the invention, $R^1$, $R^2$, $R^5$, $R^3$, and $R^{15}$ are hydrogen; $R^3$ is {—}OCH$_3$; and $R^6$, $R^7$, and $R^{17}$ are methyl.

In still another aspect of the invention, the compound comprising Formula (I) may be dihydrosinomenine and the compound comprising Formula (IV) may be (+)-thebaine.

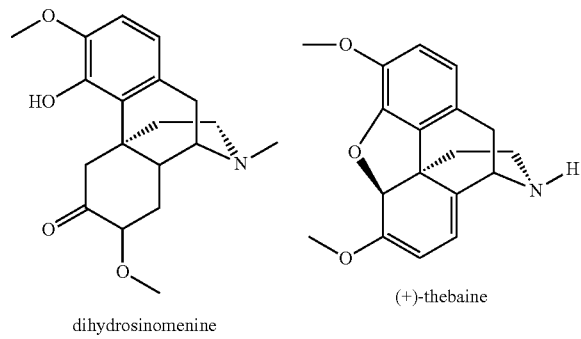

dihydrosinomenine (+)-thebaine (a) Formation of a Compound Comprising Formula (V) from the Compound Comprising Formula (I)

In one embodiment, the compound comprising Formula (I) may be transformed to a compound comprising Formula (V) through ring formation of the compound comprising Formula (I) as described in Section (I)(a)(i)-(v).

(b) Formation of a Compound Comprising Formula (X) from the Compound Comprising Formula (V)

In another aspect, the process provides a compound comprising Formula (X) by reaction of the compound comprising Formula (V) with a bromination reagent. The reaction to form the compound comprising Formula (X) may be conducted with the organic layer produced in formation of the compound comprising Formula (V) described in Section (III)(a). The reaction to form the compound comprising Formula (X) may be conducted on the resulting organic layer from the synthesis of the compound comprising Formula (V) without isolation of the compound comprising Formula (V).

(i) Bromination Reagent

The reaction to form the compound comprising Formula (X) from the compound comprising Formula (V) involves contacting the compound comprising Formula (V) with a bromination reagent. Preferably, the bromination reagent imparts a bromine atom over the double bond to result in the compound comprising Formula (X). The bromination reagent may be chosen from bromination reagents known in the art including, but not limited to, bromine, N-bromosuccinimide, pyridinium tribromide, 1,8-diazabicyclo[5.4.0]undec-7-ene hydrotribromide, benzyltrimethyl ammonium bromide, and the like.

(ii) Reaction Conditions

The process may further comprise a solvent for the reaction with the bromination reagent. Examples of solvents include those listed in Section (I)(a)(iii).

In one embodiment the solvent is an alcohol solvent chosen from methanol, ethanol, isopropanol, and propanol. In one preferred embodiment, the solvent is methanol.

The reaction may further comprise a proton donor. The proton donor may be chosen from those listed in Section (I)(a)(ii). In a preferred embodiment, the proton donor is methanesulfonic acid.

The time and temperature of the reaction between the compound comprising Formula (V) and the bromination reagent can vary depending on the bromination reagent chosen. In some embodiments, the reaction is performed at a temperature ranging from about −20° C. to about 80° C. In alternate embodiments, the reaction is conducted at about 0° C., about 10° C., about 25° C., about 50° C., about 65° C. or about 80° C. In a preferred embodiment, the reaction is performed at about 63° C. The timing of the reaction can and will vary. In some embodiments, the reaction may be conducted over the course of about 30 minutes. In still other embodiments; the reaction may be conducted over the course of about 5 hours. In a preferred embodiment, the reaction may be conducted over the course of about 3 hours.

(iii) Protection

In some aspects of the invention, the reaction may further comprise protection of the C-6 ketone group of the compound comprising Formula (V). In some embodiments, protection occurs at the same time as the bromination reaction. In particular embodiments, reaction with the solvent provides protection to the C-6 group in the form of an alkoxy protecting group. In other embodiments, the protection may be conducted as described in (II)(b)(i).

(iv) Extraction

The process may further comprise one or more extractions as described in either Section (I)(a)(v) or Section (II)(a)(iv).

(c) Formation of a Compound Comprising Formula (IV) from the Compound Comprising Formula (X)

In another aspect, the process provides a compound comprising Formula (IV) by reaction of the compound comprising Formula (X) with a proton acceptor. The reaction to form the compound comprising Formula (X) may be conducted on the organic layer resulting from the synthesis of the compound comprising Formula (X) without isolation of the compound comprising Formula (X).

The proton acceptor may be chosen from the proton acceptors listed in Section (I)(b)(i). In one embodiment, the proton acceptor can be chosen from alkoxide proton acceptors. In a preferred embodiment, the proton acceptor is potassium t-butoxide. The amount of proton acceptor can vary without departing from the scope of the invention.

(i) Reaction Conditions

The reaction conditions can and will vary. In one embodiment, the reaction conditions may be performed at temperatures ranging from about 20° C. to about 120° C. In some embodiments, the reaction may be performed at a temperature from about 60° C. to about 100° C. For instance, the reaction may be conducted at a temperature of about 60° C., about 70° C., about 80° C., about 90° C., or about 100° C.

The process may further comprise a solvent for the reaction with the proton acceptor. Non-limiting examples of solvents are described in Section (I)(a)(iii).

(ii) Extraction

The process may further comprise one or more extractions between an organic solvent and water as described in either Section (I)(a)(v) or Section (II)(a)(iv).

The yield and purity of the compound comprising Formula (IV) may vary depending on the reaction conditions. The yield generally ranges from about 40% to about 60%. In some embodiments, the yield may be above about 50%, or above about 60%. The purity of the compound may vary. In some embodiments, the purity of the compounds is above about 85%, or above about 90%, or above about 95%.

In some embodiments, the process may give the compounds in a particular configuration. The C-5, C-9, and C-13 carbons of the compound comprising Formula (IV) or the salts thereof may be either (R) or (S), so long as both C-15 and C-16 are on the same face of the molecule. In one embodiment, the C-5, C-9, and C-13 stereocenters of the compound comprising Formula (IV) or the salts thereof is chosen from chosen from RRR, RRS, RSS, RSR, SRS, SRR, SSR, and SSS, respectively. In another embodiment, the C-5, C-9, and C-13 stereocenters are chosen from RRS, SRS, RSR and SSR, respectively. In another embodiment, the C-5, C-9, and C-13 stereocenters of the compound comprising Formula (IV) or the salt thereof are RRR, respectively. In yet another embodiment, the C-5, C-9, and C-13 stereocenters of the compound comprising Formula (III) or the salt thereof are SSS, respectively.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The term "enrichment" means an amount above the statistical distribution if all chiral centers had an equal probability of being alpha or beta.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "epoxy" or "epoxide" as used herein means a cyclic ether. The ring structure generally comprises from 2 to 5 carbon atoms in the ring.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

Having described the invention in detail, it will be apparent that modifications and variations are possible without departing from the scope of the invention defined in the appended claims.

EXAMPLES

Example 1

Conversion of Compound 1 to Compound 5

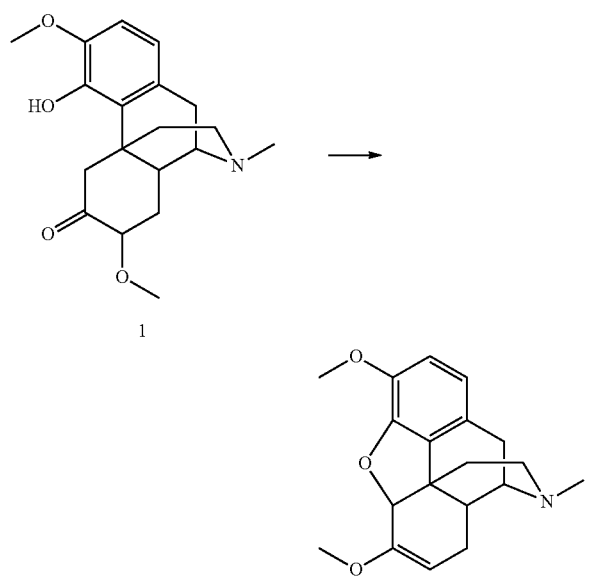

Dihydrosinomenine (compound 1) (332.1 g; 1 mol) was combined with methanol (165 mL), acetonitrile (1499 mL) and trimethyl orthoformate (219 ml; 2 mol) in a flask and stirred under nitrogen. Methane sulfonic acid (MeSO₃H) (194.6 ml; 2 mole) was added over 15 minutes to form a solution. The flask contents were heated at 63° C. for 2 hours and then heated to distill off 1160 mL of solvent. Acetonitrile (850 mL) and methane sulfonic acid (64.8 mL) were added and then 850 mL of solvent was distilled off. Acetonitrile (850 mL) and methane sulfonic acid (64.8 mL) were added and then 1000 mL of solvent was distilled off. The flask contents were cooled and produce 1035 g of compound 5 in 60%.

Example 2

Conversion of Compound 5 to Compound 6

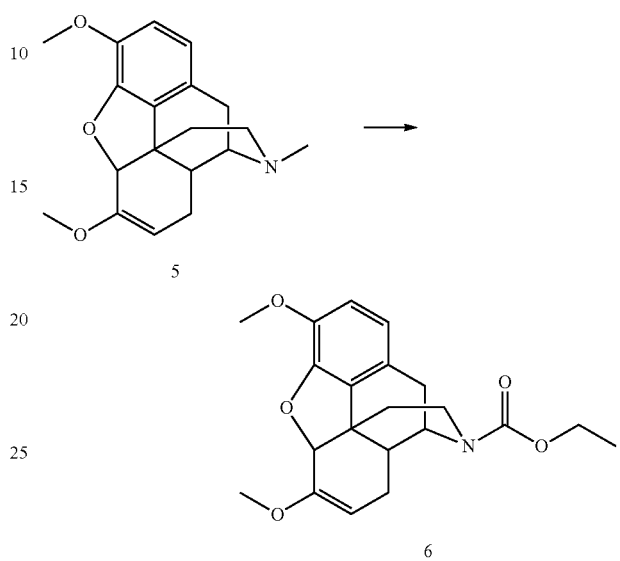

The solution from Example 1 (276 g) was added to a sodium hydroxide solution made from 120 g of a 50% sodium hydroxide and 300 mL of water to form a precipitate. Toluene (300 g) was added and heated to 68° C. while stirring. The solution was allowed to separate into two layers. The two layers were isolated and the organic layer was washed twice with water (500 mL×2). The organic layer was then heated under reflux using a distillation trap (Dean Stark). The solution was cooled below 38° C.

Sodium bicarbonate (39 g) was added to the solution and the solution was stirred under a nitrogen blanket. Ethyl chloroformate (46 g; 0.5 mol) was added drop-wise to the mixture over a period of 1.5 h. The resulting solution was heated for an additional 30 minutes. The solution was diluted with 400 mL of water and stirred at 63° C. for 30 min, and then allowed to separate into two layers. The two layers were isolated, and the organic layer was washed with 1% acetic acid (300 mL) and water (300 mL). The organic layer contained compound 6.

Example 3

Conversion of Compound 6 to Compound 2

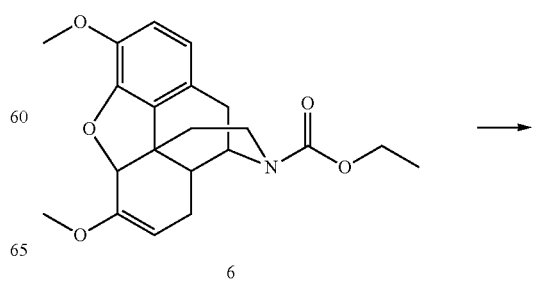

-continued

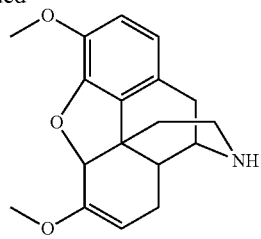

2

Dimethyl sulfoxide (DMSO) (85 mL) and 1,2-propyldiol (85 mL), and 50% NaOH (43 g) were added to the final solution of Example 2. The mixture was heated to distill off solvent until the reaction mixture reached 120° C. and was held at 120° C. for 3 hours, then cooled to 75° C. Toluene (300 mL) and water (500 mL) were added to the solution. The mixture was stirred at 75° C. for 20 minutes and allowed to separate into two layers. The aqueous layer was extracted with toluene (170 mL). The combined organic layers were washed twice with water (400 mL). The product (compound 2) was in the toluene solution.

Example 4

Isolation of the Salt of Compound 2

Half of the final toluene solution of Example 3 was stirred with isopropyl alcohol (IPA) (60 mL). 48% HBr in water was added drop-wise to the solution until a pH of 3 was obtained. The solution was stirred at 20° C. for 2 hours and filtered. The solids obtained were washed three times with IPA (20 mL×3), dried in a vacuum oven at 60° C. for 18 h to give 21.03 g of the produce, compound 2.HBr. The overall yield was 43% form compound 1.

Example 5

Conversion of Compound 5 to Compound 7

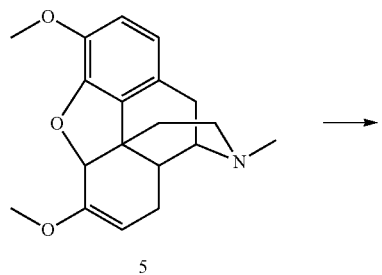

5

A portion of the final solution in Example 1 (276 g) was transferred into a flask. 1,2-ethane diol (48 g) was added. The mixture was stirred for 30 min. The resulting solution was added to a solution made from 120 g of 50% NaOH and water (300 mL). Toluene (300 g) was added and the resulting solution was heated to 68° C. while stirring. The solution was allowed to separate into two layers, which were then isolated. The organic layer was washed twice with water (500 mL×2). The organic layer was then heated to reflux to and distilled using a Dean Start apparatus to remove water. The solution was cooled below 38° C. The solution contained compound 7.

Example 6

Conversion of Compound 7 to Compound 8

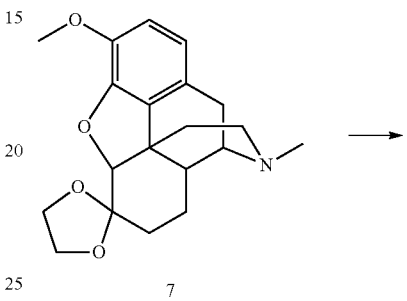

7

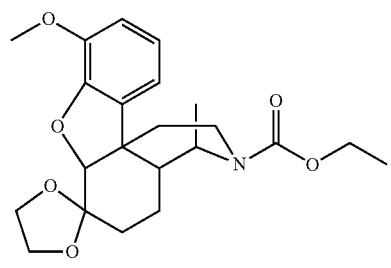

8

Sodium bicarbonate (39 g) and ethyl chloroformate (52 g) were added to the final solution from Example 5. The resulting solution was heated and stirred under nitrogen for 3 hr at 38° C. to 63° C. Water (400 mL) was added, the solution was stirred at 63° C. for 30 min and then allowed to separate into two layers. The two layers were isolated and the organic layer was washed with a 1% aqueous acetic acid solution (300 mL) and water (300 mL). The organic layer contained compound 8.

Example 7

Conversion of Compound 8 to Compound 9

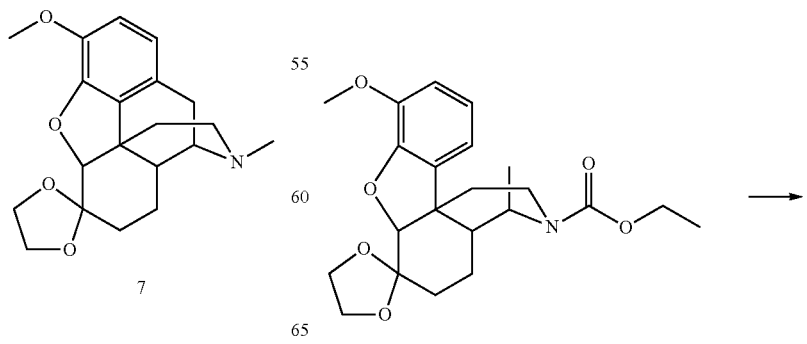

8

-continued

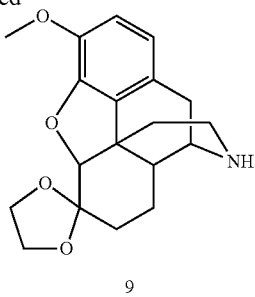

9

To the final solution from Example 6, DMSO (85 mL), 1,2-propyldiol (85 mL) and 50% NaOH (43 g) were added. The resulting solution was heated to distill off solvent until the solution reached 120° C. and was held at 120° C. for 3 hr. The solution was cooled to 75° C. Toluene (300 mL) and water (500 mL) were added to the solution. The solution was then stirred at 75° C. for 20 min and allowed to separate into two layers. The aqueous layer was extracted with toluene (170 mL) and the combined organic layers were washed twice with water (400 mL×2). Compound 9 was in the toluene solution.

Example 8

Conversion of Compound 9 to Compound 3 and Isolation of the Salt of Compound 3

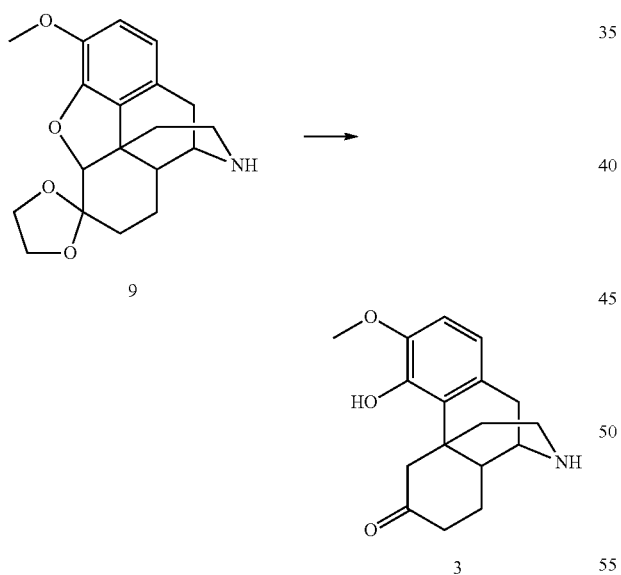

The organic layer from Example 7 was heated to 68° C. and 10% $H_2SO_4$ in water (250 mL) was added. The resulting solution was stirred at 68° C. for 10 to 15 minutes and was allowed to separate into two layers. The two layers were isolated and the aqueous layer was heated at 85° C. for 10-15 min then cooled to 40° C. NaBr (50 g) was added to the solution and the solution was cooled to 3° C. for 2 hr then filtered. The solids obtained were washed twice with 5% HBr in water (20 mL×2). The wet solids (63.8 g) were dried at 65° C. in a vacuum over night to give 52.06 g of compound 3.HBr.

What is claimed is:

1. A process for producing a compound comprising Formula (II) or salt thereof, the process comprising:
    a. contacting a compound comprising Formula (I) with a ring forming agent and a proton donor to form a compound comprising Formula (V);
    b. contacting the compound comprising Formula (V) with $R^{16}OCOX$ to form a compound comprising Formula (VI); and
    c. contacting the compound comprising Formula (VI) with an hydrolysis agent to form the compound comprising Formula (II) according to the following reaction scheme:

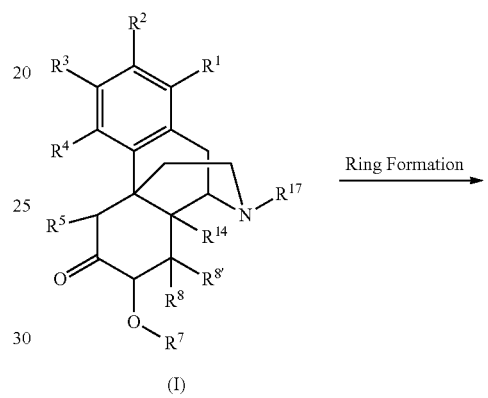

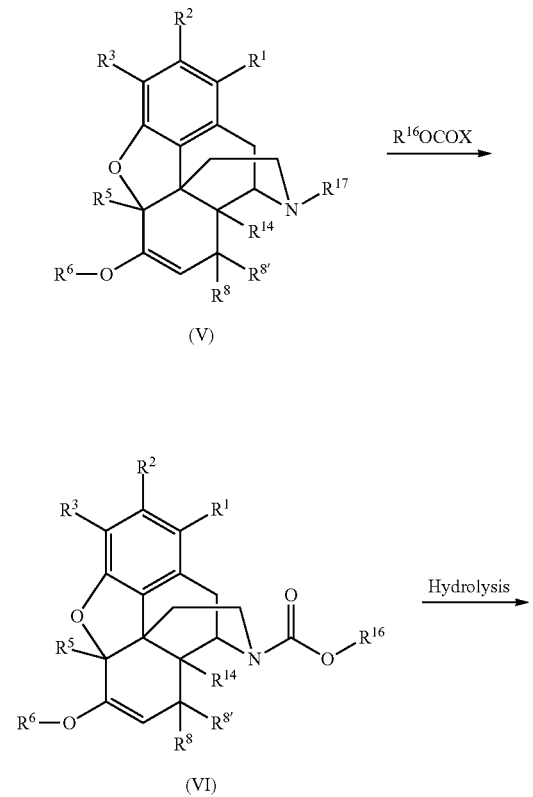

-continued

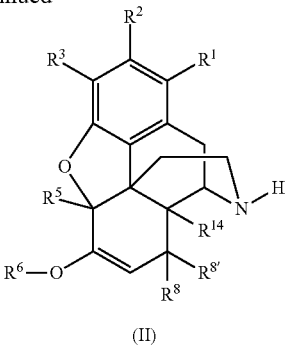

(II)

wherein no intermediates are isolated and,
$R^1$, $R^2$, $R^3$, $R^5$, $R^8$, and $R^{8'}$ are independently chosen from hydrogen, hydrocarbyl, substituted hydrocarbyl, halogen, and {—}$OR^{15}$;
$R^4$ is {—}$OR^{15}$;
$R^6$, $R^7$, $R^{16}$, and $R^{17}$ are independently chosen from hydrogen, hydrocarbyl and substituted hydrocarbyl;
$R^{14}$ is chosen from hydrogen, and {—}$OR^{15}$;
$R^{15}$ is chosen from hydrogen, hydrocarbyl, and substituted hydrocarbyl; and
X is chosen from fluorine, chlorine, bromine, and iodine.

2. The process of claim 1, wherein $R^3$ is alkyl or alkoxy; and $R^6$, $R^7$, $R^{16}$, and $R^{17}$ are independently alkyl or substituted alkyl.

3. The process of claim 1, wherein the ring forming agent is an orthoester chosen from an orthoformate and an orthoacetate; the proton donor has a pKa of less than about 6; and step (a) is conducted in the presence of a polar organic solvent and at a temperature from about 40° C. to about 80° C.

4. The process of claim 1, wherein $R^{16}$ is methyl, ethyl, or propyl; X is chlorine or bromine; and step (b) is conducted at a temperature from about 0° C. to about 100° C.

5. The process of claim 1, wherein the hydrolysis agent is a proton acceptor having a pKa greater than about 7; and step (c) is conducted at a temperature from about 60° C. and about 140° C.

6. The process of claim 1, wherein further comprising at least one solvent extraction step to yield an aqueous phase and an organic phase, the organic phase containing the reaction product.

7. The process of claim 1, wherein $R^1$, $R^2$, $R^5$, $R^8$, $R^{8'}$, $R^{14}$ and $R^{15}$ are hydrogen; $R^3$ is {—}$OCH_3$; $R^6$, $R^7$, and $R^{17}$ are methyl; the ring forming agent is trimethyl orthoformate; the molar ratio of the compound comprising Formula (I) to trimethyl orthoformate is about 1:2; the proton donor is methane sulfonic acid; step (a) is conducted in the presence of methanol and acetonitrile as a solvent and at a temperature of 60-65° C. to yield a reaction mixture containing the compound comprising Formula (V); the reaction mixture containing the compound comprising Formula (V) is extracted with toluene to obtain an organic phase containing the compound comprising Formula (V); to the organic phase containing the compound comprising Formula (V) is added the compound comprising $R^{16}OCOX$, wherein $R^{16}$ is ethyl and X is chlorine; the molar ratio of the compound comprising Formula (I) to the compound comprising $R^{16}OCOX$ is about 1:0.5; step (b) is conducted at a temperature of 60-65° C. to yield a reaction mixture containing the compound comprising Formula (VI); the reaction mixture containing the compound comprising Formula (VI) is extracted with water to obtain an organic phase comprising the compound comprising Formula (VI); to the organic phase comprising the compound comprising Formula (VI) is added sodium hydroxide as the hydrolysis agent, and a solvent mixture of dimethylsulfoxide and 1,2-propyldiol; step (c) is conducted at a temperature of about 120° C.; and the compound comprising Formula (II) or salt thereof has a yield of at least 40%.

8. The process of claim 1, wherein the C-5, C-9, C-13, and C-14 stereocenters of the compound comprising Formula (II) or the salt thereof are chosen from RRRR, RRRS, RRSR, RRSS, RSRS, RSRR, RSSR, RSSS, SRRR, SRRS, SRSR, SRSS, SSRS, SSRR, SSSR, and SSSS, respectively.

9. The process of claim 1, further comprising contacting the compound comprising Formula (II) or salt thereof with a hydrolysis agent to form a compound comprising Formula (III) or salt thereof:

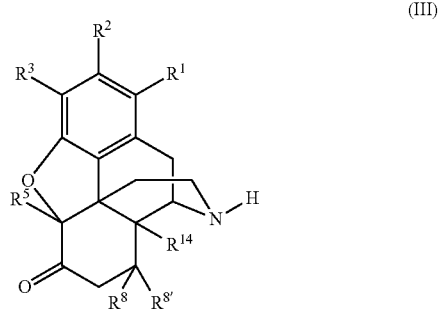

(III)

wherein $R^1$, $R^2$, $R^3$, $R^5$, $R^8$, $R^{8'}$, and $R^{14}$ are as defined in claim 1.

* * * * *